(12) United States Patent
Shine et al.

(10) Patent No.: US 6,504,006 B1
(45) Date of Patent: Jan. 7, 2003

(54) **SUBSTRATE PEPTIDES AND ASSAYS FOR DETECTING AND MEASURING PROTEOLYTIC ACTIVITY OF SEROTYPE A NEUROTOXIN FROM *CLOSTRIDIUM BOTULINUM***

(76) Inventors: Nancy Rose Shine, 2175 Chuleta Ct., Los Altos, CA (US) 94024; Karen Renée Crawford, 14082 Taos Dr., Saratoga, CA (US) 95070; Linda Jo Ann Eaton, 1341 De Loach Ct., San Jose, CA (US) 95125

( * ) Notice: Subject to any disclaimer, the term of this patent is extended or adjusted under 35 U.S.C. 154(b) by 0 days.

(21) Appl. No.: 09/976,535

(22) Filed: Oct. 12, 2001

(51) Int. Cl.[7] .............. A61K 38/04; C07K 16/00; C07K 17/00; C07K 5/00; G01N 33/53
(52) U.S. Cl. .............. 530/323; 530/327; 435/975
(58) Field of Search .............. 530/323, 327; 435/975

(56) References Cited

U.S. PATENT DOCUMENTS 5,965,699 A 10/1999 Schmidt

OTHER PUBLICATIONS

Christine Anne, et al., High_Throughput Fluorogenic Assay for Determination of Botulium Type A Neurotoxin Protease Activity, Analytical Biochem, vol. 291, p253–261 Mar. 9, 2001.

*Primary Examiner*—Mark Navarro
(74) *Attorney, Agent, or Firm*—Intellectual Property Law Offices of S. Alex Liao; S. Alex Liao (57) ABSTRACT

Substrates for detecting and measuring the proteolytic activity of botulium type A neurotoxin in an assay are described. Detection is based on an increase in fluorescence due to hydrolysis of these internally quenched fluorescent peptide substrates by botulium type A neurotoxin. Several 13–15 amino acid peptides, derived from the substrate region of SNAP-25, have been constructed and analyzed for use in the assay.

8 Claims, 3 Drawing Sheets

SUBSTRATE PEPTIDES AND ASSAYS FOR DETECTING AND MEASURING PROTEOLYTIC ACTIVITY OF SEROTYPE A NEUROTOXIN FROM *CLOSTRIDIUM BOTULINUM*

INTRODUCTION

The present invention generally relates to a group of fluorescent peptides for detecting the enzymatic activity of botulinum toxin type A.

Seven immunologically distinct botulinum neurotoxins, types A, B, C, D, E, F, and G are produced by the anaerobic bacterium *Clostridium botulinum*. Synthesized as a single 150 kD polypeptide chain in the bacteria, these neurotoxins are subsequently cleaved to produce two chains, a heavy chain and a light chain, which are linked by a disulfide bond. For each toxin, the 50 kD light (L) chain is a zinc-dependent protease, which cleaves a single target protein essential for synaptic vesicle membrane fusion during neurotransmission. Cleavage of the target protein inhibits neurotransmitter release among neurons, which leads to muscular paralysis [Bigalke and Shoer, (1999) In:Handbook of Experimental Pharmacology, Vol. 145 Bacterial Protein Toxins (K. Aktories and I. Just, Eds.) pp.407–443, Springer-Verlag, Berlin]. All references cited herein supra and infra are hereby incorporated in their entirety by reference thereto.

Clinically, there are three forms of this neuroparalytic disease: food borne, infant and wound botulism. As little as 30–100 ng of the neurotoxin is potentially lethal to humans. Thus, detection of these toxins requires a highly sensitive and reliable assay. In addition, botulinum neurotoxins are increasing useful clinically as an active ingredient in therapeutic agents. Again, sensitive and accurate potency assays are essential to assure toxin quantity, activity, and safety in any given therapeutic formulation. Currently the mouse bioassay is the "gold standard" for the measurement and standardization of these neurotoxins. While this in vivo assay has the prerequisite sensitivity with a detection limit of 10–20 pg neurotoxin for the most active toxin serotype, there are a number of major drawbacks. 1) The method requires the use of a large number of animals for initial detection for typing by neutralization tests and for toxin quantitation. 2) The method is costly largely due to the expense incurred for the maintenance of animal facilities. 3) The method is slow and taking up to 4 days for completion. 4) The method lacks specificity and is not reliable if the sample contains other lethal substances. 5) The method is performed by a limited number of laboratories.

Considerable efforts have been expended in the development of suitable alternative in vitro assays. Several laboratories have developed ELISA-type assays with sensitivities comparable to the mouse bioassay [Pearce et al (1997) *Toxicon* 35:1373–1412; Szilagyi et al (2000) *Toxicon* 38: 381–389]. However, these assays are based on immunodetection, and as such may not distinguish active from inactive toxin, a crucial limitation. Additionally, immunodetection may not reveal novel toxins constructed from the enzymatic portion of botulinum toxin and a binding domain of another protein. The discovery that all seven neurotoxin serotypes contain a zinc endoprotease and the identification of the specific protein substrates and cleavage sites recognized by each serotype, provides a potentially sensitive and direct means for monitoring the presence of toxin [Fujii et al (1992) *Toxicon* 30:1486–1488; Schiavo et al (1993) *Trends Microbiol* 1:170–174; Blasi et al (1993) *Nature* 365:160–163]. Investigations using synthetic substrates derived from synaptosome-associated protein (SNAP-25) for botulinum toxin type A and derived from vesicle-associated membrane protein (VAMP-2) for type B, demonstrated that cleavage products could be observed using RP-HPLC [Shone et al (1993) *Eur. J. Biochem.* 217:965–971; Schmidt and Bostian (1997) *J. Prot. Chem.* 16:19–26]. This method, however, does not allow for detection of small quantities of toxin. An in vitro endopeptidase assay has been described that is as sensitive as the mouse bioassay for detection of botulinum toxin type A [Ekong et al (1997) *Microbiology* 143:3337–3347]. The approach involves the use of antibodies directed to the neurotoxin-cleaved substrate. The assay is limited by the need for specific reagents and requires a multi step process consuming considerable time as is characteristic of ELISA assays.

A U.S. Pat. No. 5,965,699 ("'699 patent") by Schmidt et al describes and claims a sensitive assay to detect cleavage of peptide substrates by botulinum toxin type A. The method uses fluorescamine to detect primary amines newly created by hydrolysis of the substrates. Using purified toxins, this method works well for tests, such as screening for potential inhibitors. However, if test samples involving food products or serum contain other sources of primary amines, such as contaminating proteins, the contaminating proteins may generate high background in the tests. The high background would hinder the detection of small quantities of toxin.

A classic approach for measuring the activity of proteolytic enzymes utilizes short, di-and tripeptide substrates which contain a chromophore or fluorophore moiety at the site of cleavage [Castillo et al (1979) *Anal. Biochem.* 99:53]. The chromophore or fluorophore is attached to the C-terminal of a short di- or tri-peptide through acylation which changes the electronic properties. Subsequent cleavage of the substrate and deacylation of the chromophore/fluorophore gives rise to a measurable spectrophotometric change proportional to the extent of hydrolysis. These assays do not require separation of the cleavage products. They are highly sensitive, generally relatively fast and simple to perform. However, because of the demanding substrate recognition requirements of the botulinum toxins, there are two formidable problems. First, if the neurotoxins require large peptide substrates for efficient cleavage, di- or tri-peptides would not be recognized by the neurotoxin. Secondly, and most importantly, hydrolysis of a given substrate only occurs for those peptides that contain appropriate amino acids spanning both sides of the cleavage site. Substitution of a chromophore in close proximity to the cleavage site, which is necessary when using this technique, would eliminate hydrolysis.

More recently, an alternative approach, based on intramolecularly quenched fluorescent substrates has been successfully utilized to characterize various peptidases [Szollosi et al (1998) *Cytometry* 34:159–179]. These fluorogenic substrates contain a fluorescent group at one end and a suitable chromogenic group that can quench the fluorescence at the other. Substrates may be designed to include amino acids on either side of the enzymatically hydrolyzed bond. The fluorescent signal in the uncleaved substrate is quenched by fluorescence resonance energy transfer (FRET) between the fluorophore and quencher groups. Efficiency of quenching depends on i) the distance between the donor/acceptor groups, the shorter the distance the more efficient the quenching, and ii) the extent to which the emission spectrum of the fluorophore and the absorbance spectrum of the chromophore overlap [Yaron et al (1979) *Anal. Biochem.* 95:228–235]. The greater the spectral overlap a given donor/ acceptor pair has, the more efficient the quenching of the signal will be. Full fluorescence is restored after cleavage of the peptide. Hence, enzymatic activity can be monitored continuously by recording the increase in fluorescence intensity with time.

A similar intramolecularly quenched fluorescent substrate is described and successfully used for determining botulinum toxin type B protease activity [Anne et al (2001) Anal. Biochem. 291:253–261]. The 34 amino acid substrate described is a contact quenched peptide. The mechanism of quenching is not by FRET, but is collisional. For these contact quenched substrates, the fluorophore and quencher must be in close proximity. In this substrate, they are separated by only four amino acids. Even though the modified amino acids are quite close to the cleavage site, this peptide substrate is still recognized by the neurotoxin. A similar substrate specific for tetanus toxin, however, was not cleaved, indicating that the positioning of the fluorophore and quenching groups is crucial in constructing a suitable substrate and emphasizing that the design of useful fluorescent substrates is not trivial.

In this invention, we describe a series of FRET substrates for botulinum toxin type A (BTA). It has been shown previously that a 17-amino acid peptide from the SNAP-25 target protein is hydrolyzed as efficiently as the full substrate [Schmidt and Bostian (1995) J. Prot. Chem. 14:703–708]. It was also noted that, while reduction to a 13 amino acid substrate decreased the hydrolysis by 43%, this peptide was still a good substrate [Schmidt and Bostian (1997) ibid.]. If the FRET pairs are separated by 17 amino acids, quenching would be minimal. Thus we have designed and synthesized thirteen 13–15 amino acid peptides using three different FRET pairs, o-aminobenzoyl (Abz)/2,4 dinitrophenyl(Dnp), Abz/3-nitro-tyrosine, and (7-methoxycoumarin-4-yl)acetyl (Mca)/Dnp. One substrate containing Mca/Dnp and some of the substrates containing Abz/Dnp, were cleaved by the toxin, indicating that these FRET pairs do not interfere with binding and cleavage and that this method is feasible.

In this invention, we describe the design, construction, catalytic properties and overall evaluation of 13 new FRET peptide substrates for assessing the protease activity of botulinum toxin type A. These substrates may be used in a highly sensitive, rapid and relatively inexpensive in vitro assay for 1) detecting low levels of toxin contamination in food, clinical, and environmental samples, 2) evaluating the quantity and safety of therapeutic agents containing botulinum toxin type A, 3) monitoring the production of botulinum toxin type A by fermentation processes, 4) detecting toxin neutralizing antibodies, as well as 5) screening and characterization of a large number of toxin inhibitors, which are potential therapeutic agents.

SUMMARY OF INVENTION

The present invention relates to a new type of peptide substrate for the determination of the endoprotease activity of C. botulinum type A neurotoxin. It is well known that fluorescent dyes absorb light energy and emit it at a lower energy producing fluorescence. If a second chromophore is within a certain distance of the dye and absorbs light at the wavelength of the emitted light, then the absorbed light can be transferred to the second chromophore. In other words, the second compound or acceptor quenches the light emitted by the first compound or donor. The process is referred to as Fluorescence Resonance Energy Transfer (FRET). A pair of compounds which interact in this matter as a donor and acceptor is called a FRET pair. The effectiveness of this technique depends on the distance between the FRET pair as well as the amount of overlap between the emission spectrum of the donor and the absorption spectrum of the acceptor. The efficiency of energy transfer between the donor and acceptor is inversely related to the sixth power of the distance between the two. When the FRET pair on a single peptide is separated due to cleavage of the peptide, a change in the fluorescent emission occurs. In this case, light absorbed by the donor is emitted at a longer wavelength and is detected using a fluorimeter. For a review see Wu and Brand (1994) Biochem, 218, 1–13.

The present invention describes a peptide suitable for digestion by a specific protease as well as a method using both peptides and antibodies to selectively detect the C. botulinum type A endoprotease if other proteases are present. Utilizing the known sequence of the cleaved area of SNAP 25, relatively short peptides were designed to include amino acid substitutions intended to decrease the suitability as a substrate for other proteases while maintaining its function as a substrate for botulinum type A toxin. Additionally, several FRET pairs were bound to these peptides to determine which would provide a minimum of background fluorescence and maintain the susceptibility of the peptide to digestion by C. botulinum type A endoprotease.

Historically, antibodies have been used to distinguish the seven different serotypes of C. botulinum. Monoclonal antibodies specific to different regions of C. botulinum neurotoxin type A have been described [Hallis et al (1993) In: Botulinum and Tetanus Neurotoxins (B. R. DasGupta, Ed.) pp. 433–436, Plenum Press, New York; Pless et al (2001) Infect. Immun. 69:570–578; Wu et al (2001) Appl. Environ. Microbiol. 67:3201–3207]. The peptide substrates described in this invention specifically detect the protease activity of the light chain of C. botulinum type A. Elimination of the protease activity by an antibody directed to the enzymatic portion of the neurotoxin creates a highly specific method of identification.

In addition, Botulinum neurotoxins have several properties which allow them to be seperated from a sample containing other materials including other proteases. Examples of such properties include the fact that the neurotoxin will adhere to chromatography media or precipitate as described in the classical purification schemes [DasGupta and Sathyamoorthy (1984) Toxicon 22:415–424]. Botulinum toxins may also be captured using a solid state bound antibody [Wictome et al (1999) FEMS Immunology and Medical Microbiology 24:319–323].

Therefore, it is an object of the present invention to provide substrate peptides for use in an assay for determining the enzymatic activity of botulinum type A neurotoxin. Such substrates must be carefully designed to meet the demanding requirements of the serotype A neurotoxin. Selection of an efficient donor/acceptor pair is critical for maximum quenching in the uncleaved substrate. In turn, this FRET pair must not interfere with recognition, binding, or catalysis by BTA.

It is another object of the present invention to provide a method for measuring and detecting the proteolytic activity of botulinum type A neurotoxin in a sample. This method may be used with a standard curve to quantitate the toxin. Alternatively, the method may simply be used for a qualitative determination of the presence of the toxin. This method may be applied to monitoring the production of botulinum type A toxin in fermentation. The method can also be used in evaluating the quantity and safety of therapeutic agents containing botulinum type A toxin. The specificity of the assay described in the present invention can further be increased by first enriching the concentration of neurotoxin by using chromatography media or precipitation. The neurotoxin in a sample can also be captured using a solid state bound antibody.

It is further an object of the present invention to provide a method for screening large numbers of inhibitors against botulinum type A toxin or compounds that have stimulatory characteristics to botulinum type A toxin. Inhibitors may be useful in treating patients with botulinum type A intoxication, while the stimulatory compounds may be used to enhance the activity of neurotoxin-containing drugs.

DETAILED DESCRIPTION

The present invention relates to the design of FRET substrates to be used to detect and quantitate botulinum toxin endoprotease activity. The proteolytic activity of BTA is monitored by measuring the increase in fluorescence intensity of the substrates in the presence of toxin. These FRET substrates permit the rapid assay of many samples in a high through-put screening format. The assay is highly sensitive, permitting the accurate measurement of as little as 2.6 ng/ml toxin. These FRET substrates are suitable for a simple, relatively inexpensive, sensitive, and specific assessment of BTA activities from a number of sources. These sources include contaminated food products, environmental and clinical samples, samples containing toxins to be used therapeutically, samples from the fermentation of *Clostridium botulinum* producing the toxin, samples containing toxin type A antibodies, samples containing potential inhibitors.

The two main objectives in the design of a suitable FRET substrate for BTA are 1) to use the minimum effective peptide substrate length required for hydrolysis in order to optimize the quenching efficiency and 2) to choose an acceptor/donor pair that would not interfere with binding and catalysis and that could be easily attached to the peptide, preferably by conventional solid phase techniques.

Each botulinum neurotoxin cleaves selectively a single peptide bond in specific substrate proteins [Li et al. (1999) *Toxin Rev*.18:95–112]. Botulinum toxin type A cleaves the synaptosomal protein, SNAP-25, exclusively between residues $^{197}$Gln and $^{198}$Arg. It has been shown that a short 13-amino acid peptide consisting of residues 190–202 of the SNAP-25 substrate is hydrolyzed efficiently by BTA [Schmidt and Bostian, 1997, ibid]. All the peptides synthesized were based on this 13-amino acid sequence starting with threonine at position 190 in SNAP-25, $^{190}$T-R-I-D-E-$^{195}$A-N-Q-R-A-$^{200}$T-K-M (SEQ ID NO:1). As is routinely done with small peptide substrates and as previously suggested for these BTA substrates [Schmidt and Bostian, 1995, ibid], the C-termini of all the sequences are amidated.

The Abz/Dnp donor-acceptor pair was initially chosen for the FRET peptides. The modified Lys(Dnp) and Abz are relatively inexpensive and the peptides were easily prepared by solid phase synthesis. The o-amino benzoyl and dinitrophenyl groups are small which should reduce interference of the pair in binding. The amino acid sequences of the substrate peptides described in this study are given in Table 1. Initially, in order to minimize any structural changes to the peptide sequence, the fluorogenic group, Abz, was linked to the N-terminus, and the quenching group, Lys(Dnp), was added to the C-terminal (Table 1, SEQ ID NO:2–SEQ ID NO:8). Several substrates were synthesized with the Lys (Dnp) at position 12 (Table 1, SEQ ID NO:9 and SEQ ID NO:11–SEQ ID NO:14) in order to decrease the separation of the FRET pairs. We also examined Abz/3-nitro-tyrosine as a possible FRET pair (Table 1, SEQ ID NO:10). Since it has been shown that the SNAP-25 mutant where $^{198}$Arg is replaced by $^{198}$Tyr, is still susceptible to hydrolysis by BTA [Vadakkanchery et al., (1999) *J. Neurochem*. 72: 327–337], the 3-nitro-tyrosine was placed at position 198. This donor/acceptor pair is then only 7 amino acids apart, increasing the likelihood of additional quenching in the uncleaved peptide. Also, substitution of Arg for Tyr eliminates one potential trypsin cleavage site. A 7-methylcoumarin (Mca)/Dnp substrate (Table I, SEQ ID NO: 12) was also evaluated. This peptide is more difficult to synthesize, but it is potentially a better FRET peptide.

In another embodiment, the present invention discloses a testing kit for measuring botulium type A neurotoxin in a sample. The kit may contain vials or containers having a peptide substrate selected from peptides of SEQ ID NO. 2, 6, 7, and 9. The kit may also contain a positive control for a known amount of Type A neurotoxin, the light chain of Type A neurotoxin, or an appropriate protease, for use as a standard for the measurement of Type A neurotoxin. In addition, buffers and factors necessary for the hydrolysis can be included in the kit for the convenience of the users. The kit may also contain specific inhibitors such as antibodies to distinguish hydrolysis by BTA.

It is therefore understood that the specification, examples, and embodiments are for illustration purposes only and should not be read as limiting the scope of the claimed invention.

MATERIALS AND METHODS

Reagents and Chemicals

All buffer reagents were obtained from Sigma Chemical Co., St. Louis, Mo. Sequencing grade trypsin was obtained from Roche Diagnostics Corp., Indianapolis, Ind. Dithiothreitol was purchased from USB, Cleveland, Ohio. Dimethylsulfoxide (DMSO) was obtained from Pierce, Rockford, Ill. The FRET peptide, SEQ ID No:2, was kindly gifted to us. SEQ ID No:3 was synthesized and purified by SynPep, Dublin, Calif. All remaining FRET peptides were synthesized and purified by PeptidoGenic research & Co., Inc., Livermore, Calif. The peptides were shown to be 90% pure or greater by reverse phase HPLC on a C18 column eluted with a 10 min linear gradient of acetonitrile (15–70%) in 0.1% trifluoroacetic acid. The expected molecular weights were obtained by mass spectrometry. The peptides were supplied as the C-terminal amides, as requested. Horse anti-botulinum toxin type A was from Army horse #60 serum (gift of Dr. R. H. Whitlock from the University of Penna.)

The purified botulinum toxin type A is from our laboratory, List Biological Laboratories, Inc., Campbell, Calif. When examined on 7.5%SDS-polyacrylamide gels, this product migrates as a single major band with an apparent molecular weight of approximately 150,000 daltons. In the presence of a reducing agent, the preparation migrates as two bands with apparent molecular weights of 100,000 and 50,000 daltons, as expected. Vials of BTA (10 μg) were reconstituted in 100 μl of 20 mM HEPES, pH 7.3 containing 0.2 mM ZnCl$_2$, 5 mM DTT, and 1.0 mg/ml BSA (BUFFER A) immediately prior to use. In order to reduce the toxin, the BTA solution was then preincubated for 30 min at 37° C. Reduction of the toxin by the DTT in Buffer A is necessary to promote proteolysis of the peptide substrates.

Except for SEQ ID NO:13, stock solutions of all substrates were made in DMSO. Each FRET peptide substrate was weighed and an appropriate amount of DMSO was added to make an approximately 5.0 mM stock solution. Final substrate concentrations in each stock were determined from the absorbance at 363 nm using the $\epsilon_{356nm}$=15,900 M$^{-1}$cm$^{-1}$ for LysDnp. These concentrations were used to calculate the amount of stock substrate solution to add to 3.0 ml Buffer A to obtain 7.5 μM final concentration. In order to minimize oxidation of the Met residue in SEQ ID NO:13, the later peptide was weighed and dissolved in 20 mM HEPES, pH 7.3. The final concentration was determined as described for all other FRET substrates. Since SEQ ID NO:10 contains a 3-nitro-tyrosine instead of the LysDnp, the final concentration was based on the weighed amount only.

METHODS

Fluorimetric Measurement Parameters

Fluorogenic enzyme activity assays were carried out on a Perkin Elmer LS-5B spectrofluorometer equipped with a thermostated cell holder maintained at 37° C. using a standard 3.5 ml cuvette. The hydrolysis of the Abz-peptidyl-Dnp substrates was followed using an excitation wavelength, $\lambda_{ex}$, of 326 nm and an emission wavelength, $\lambda_{em}$, of 423 nm. For the Mca/Dnp peptide substrate ke, was set to 328 mn and kel to 393 nm. The excitation bandwidth was set to 3 mn. Emission bandwidths of 5 nm and 10 nm were used.

Changes in Fluorescence Intensity

Based on the concentration of each FRET substrate as described above, an amount of the DMSO stock solution was added to 3.0 ml of BUFFER A to give a final concentration of 7.5 μM substrate. This solution was incubated at 37° C. for 15 minutes to achieve thermal equilibrium. The proteolysis reaction was initiated by addition of an appropriate amount of BTA stock solution (10 μg/1001 μl) and mixing by repeated inversion of the cuvette. The time dependent increase in fluorescence intensity (FI) was monitored at 37° C. and the initial reaction velocity, expressed in arbitrary fluorescence units per minute (FI/min) was obtained by least-square analysis of the initial part of the reaction. The fluorescence intensity measured is directly proportional to the amount of hydrolysis of each FRET peptide by BTA.

Total Enzymatic Hydrolysis

In order to determine the maximum fluorescence intensity observable for various concentrations of SEQ ID NO: 6, total enzyme hydrolysates were performed at 37° C. using 50 μM trypsin in Buffer A. The reaction was started by addition of trypsin to 2, 4, 6, 7.5, and 10 μM SEQ ID NO: 6 in 3.0 ml Buffer A. Digestion was followed for 2 hrs to insure that maximum fluorescence was achieved, Samples were diluted 1:10 with Buffer A and read using the fluorimetric measurement parameters given above with an emission slit width of 5 mn. Values shown were corrected for background fluorescence of the buffer.

Measurement of the Detection Limit

The limit of detection is the minimum concentration of BTA that can be measured with 99% confidence that the BTA present is greater than zero under our conditions using this fluorogenic assay. A calibration curve was generated by measuring the initial rate of proteolysis as a function of BTA concentration. Eight replicates of a concentration estimated to be slightly greater than the expected detection limit (6.7 ng/ml BTA) were performed. Each analysis was calculated as ng/ml using the current calibration curve. The detection limit was calculated as 2.998 (Student's t-Distribution with 99% confidence and 7 degrees of freedom) times the standard deviation of the 8 replicates.

Antibody Studies

Studies with the horse anti-botulinum antibody were performed using 0.44 nM BTA preincubated in Buffer A for 30 min at 37° C. to reduce the toxin as described above. The toxin and antibody were added to Buffer A in the cuvette and incubated for an additional 30 min at 37° C. The reaction was initiated by addition of 7.5 $\mu$M SEQ ID NO:6.

RESULTS AND DISCUSSION

BTA Proteolysis

The fluorescence monitored hydrolysis of 7.5 $\mu$M of each substrate by 9 nM BTA under conditions described in Materials and Methods is given in Table I. SEQ ID NO:2 was the first substrate utilized in this study. The uncleaved peptide was effectively quenched indicating that this 13-amino acid substrate constituted a feasible FRET peptide. Cleavage of the peptide with trypsin was accompanied by an 8-fold increase in fluorescence intensity. The peptide was readily hydrolyzed by BTA indicating that the donor/acceptor pair did not significantly interfere with binding to BTA or catalysis by the toxin. All subsequent substrates were based on this sequence.

Comparison of the FRET Peptides

The largest increase in fluorescence with time was observed for SEQ ID NO:6. This substrate contains one D-amino acid at position 2. The D-amino acids were substituted at position 2 and 12 to eliminate potential trypsin cleavage sites in the substrates (SEQ ID NO:3–5). Comparison of SEQ ID NO:5 and SEQ ID NO:6 indicates that the simple substitution of D-Lys (SEQ ID NO:5) for Lys (SEQ ID NO:6) diminishes hydrolysis by BTA. This may also explain the reduced hydrolysis of SEQ ID NO:3 and SEQ ID NO:4. The substitution of D-Arg at position 9 (SEQ ID NO:8) to eliminate this trypsin site also significantly reduced hydrolysis by BTA. This was not surprising since this Arg is at the cleavage site.

Comparing SEQ ID NO:4 and SEQ ID NO:5 suggested that substitution of Q for E at position 5 increased the rate of hydrolysis. This result was consistent with previously reported data using a similar 17-amino acid peptide [Schmidt and Bostonian, 1997, ibid.]. However, comparing the rates observed for SEQ ID NO:6 and SEQ ID NO:7, it appears that this substitution decreases hydrolysis. Subsequent peptides, SEQ ID NO:10 through SEQ ID NO:14 retained E at position 5.

In substrate, SEQ ID NO:9, the Dnp group was moved from position 14 to position 12. While the quenching was indeed more efficient, comparison of SEQ ID NO:11 with SEQ ID NO:6 indicates that the Dnp group at position 12 interferes with hydrolysis by BTA. While this peptide is not the best for studies requiring sensitivity, it could be the peptide of choice when higher concentrations of BTA are being used because it is well quenched.

Comparison of SEQ ID NO:13 with SEQ ID NO:11 and SEQ ID NO:12, suggests that substitution of methionine for norleucine at position 13 does not improve the substrate. Since methionine is readily oxidized, norleucine is the preferred amino acid.

In SEQ ID NO:14, E is substituted for Q at position 8. This substitution was examined because when Arg is flanked by an acidic amino acid the rate of cleavage by trypsin is greatly reduced. In the same mutational analysis mentioned above [Vadakkanchery et al. (1999) ibid.], it was shown that substitution of E for Q at position 197 in SNAP-25 (see SEQ ID NO: 1) did not influence the rate of hydrolysis by BTA. Again, results with the short peptide substrates do not agree. Since no hydrolysis was observed for peptide SEQ ID NO:14, this peptide could be used in conjunction with SEQ ID NO:9 as a control to monitor for non-specific cleavage, remembering that this peptide is only slowly cleaved by trypsin. Likewise, SEQ ID NO:8 could be used with SEQ ID NO:6 to test for non-specific cleavage of the peptide.

Comparison of FRET Pairs

In this invention, three different FRET pairs, Abz/Dnp, Mca/Dnp, and Abz/3-nitro-tyrosine, were investigated. The fluorescence intensities measured for a 7.5 μM sample of each peptide are shown in Table II. For the Abz/Dnp pair, peptides with the Lys-Dnp at position 12, 14 and 15 were synthesized. As expected, the quenching observed for FRET peptides with the Lys-Dnp at position 12 (SEQ ID NO:9, 11, 13 and 14) was more efficient than that observed for those containing Lys-Dnp at position 14 or 15 (SEQ ID NO:2, 3 and 4–8). Interestingly, substrates with D-lysine in position 12 were more efficiently quenched than those containing L-lysine in that position. Unfortunately, these well-quenched FRET peptides were not the best substrates. For SEQ ID NO:10, less quenching is observed even though the Abz/3-nitro-tyrosine FRET pair is closer together. Mca is another fluorophore often used successfully in FRET peptides [Knight (1995) Methods in Enzymology 248 19–34], however, in SEQ ID NO:12 where Mca was substituted for the Abz, the amount of quenching observed was minimal. The best FRET peptide that was also a good substrate for BTA was SEQ ID NO:6.

Sensitivity of SEQ ID NO:6

Figure 1:
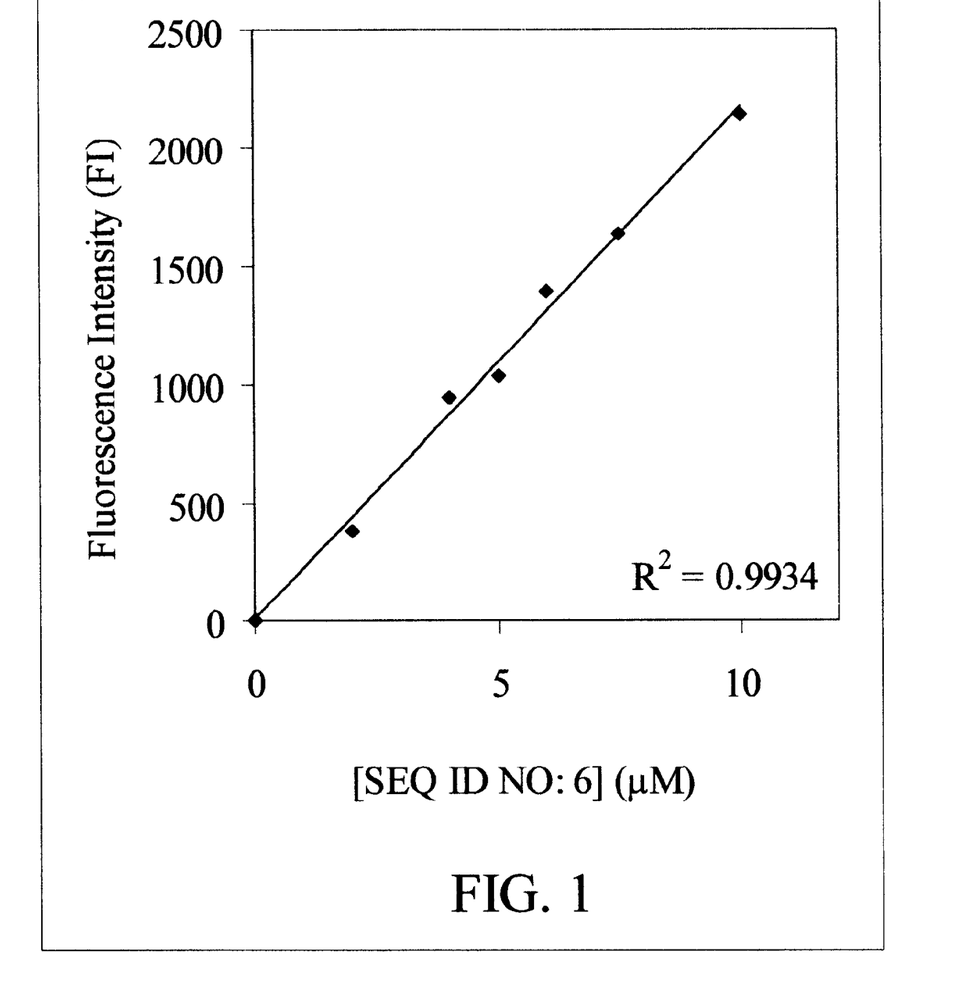
FIG. 1 represents the fluorescence intensity measured after total enzymatic hydrolysis of peptide SEQ ID NO:6 as described in Materials and Methods versus concentration of the peptide.

Since SEQ ID NO:6 was the best FRET substrate for BTA, tests to determine the sensitivity of this peptide for detection of BTA were conducted. When using FRET peptides care must be taken to insure that there is a linear dependence of fluorescence intensity on concentration within the concentration range used. When the concentration of peptide is too high, the fluorescence of the liberated Abz-containing peptide fragment will be quenched by Dnp from uncleaved fragments or from Dnp-containing product of the cleavage. This quenching artifact is known as the inner filter effect. At this point the fluorescence change upon enzymatic cleavage will be non-linear. Therefore, as a first step in evaluating the sensitivity of SEQ ID NO:6, the fluorescence intensity of a total trypsin digest for a series of SEQ ID NO:6 concentrations was established. As shown in FIG. 1, concentrations of SEQ ID NO:6 up to 10 μM are linearly related to the change in fluorescence.

Figure 2:
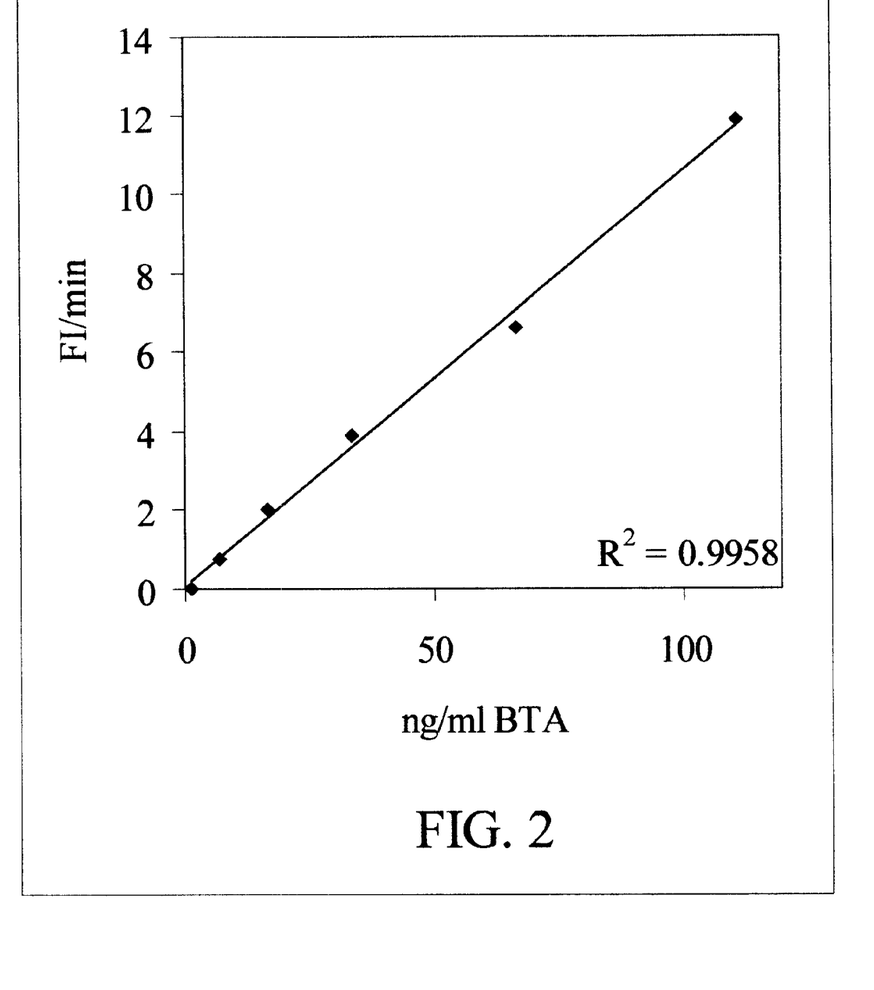
FIG. 2 represents the initial rate of change of fluorescence versus BTA concentration for the hydrolysis of 7.5 µM SEQ ID NO:6 at 37° C. as described in Materials and Methods.

The sensitivity of the fluorogenic substrate SEQ ID NO:6 was determined by evaluating the dependence of the initial velocities on BTA concentrations. The peptide substrate concentration was 7.5 μM. The results are shown in FIG. 2. There is a linear relationship between the fluorescence and BTA at concentrations up to 110 ng/ml. Between 110 ng/ml and 222 ng/ml, significant deviation from linearity ($R^2$= 0.9752) is observed. The limit of detection, obtained as described in Materials and Methods, was 2.6 ng/ml. These results indicate that under these conditions, SEQ ID NO:6 can accurately detect down to 2.6 ng/ml of purified toxin. Additionally, pure toxin concentrations up to 110 ng/ml may be determined using this substrate.

Antibody Studies

Figure 3:
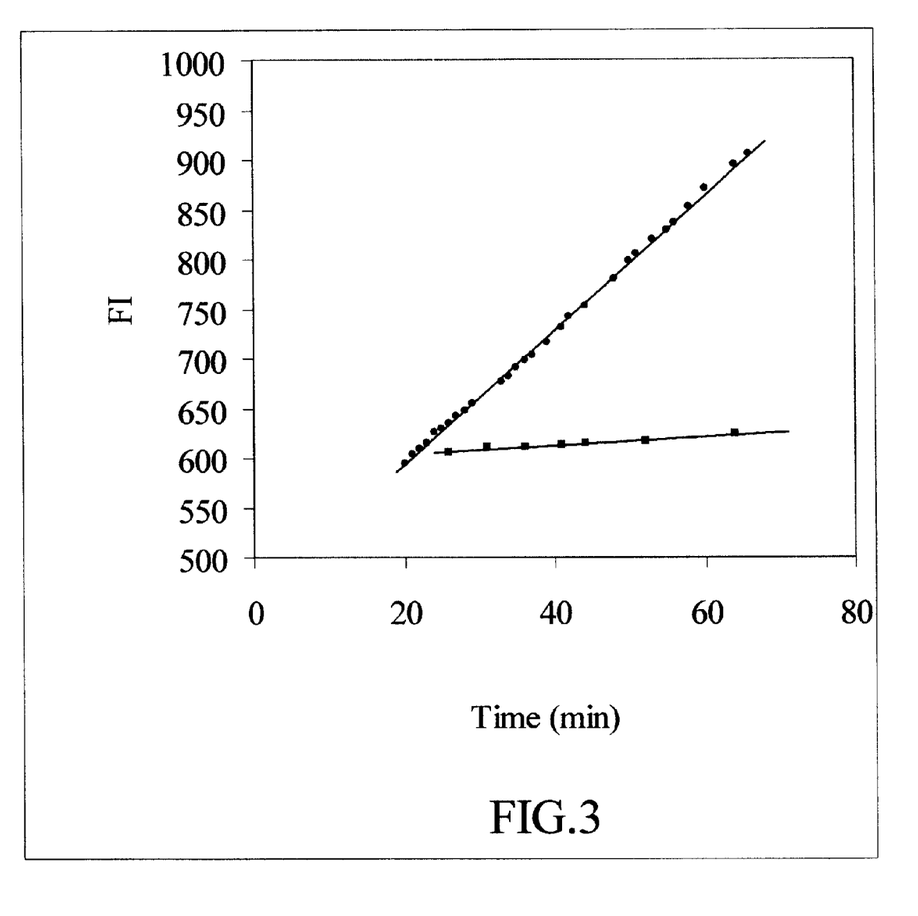
FIG. 3 represents cleavage of 7.5 µM SEQ ID NO:6 at 37° C. by 0.44 nM BTA in the absence (●-●) and presence (x-x) of 1:1000 dilution of horse anti-botulinum toxin type A antibody as described in Materials and Methods.

As suggested above, the presence of residual background protease activity can be assessed using a specific antibody capable of blocking endoprotease activity of BTA. We have examined the effect of a polyclonal antibody from horse on the cleavage of SEQ ID NO:6 by purified BTA. As shown in FIG. 3, the change in fluorescence intensity per min for 7.5 μM SEQ ID NO:6 in the presence of 0.44 nM BTA was 6.8 FI/min. In the presence of a 1:1000 dilution of the polyclonal antibody, the change in fluorescence was decreased to 0.43 FI/min. The polyclonal antibody inhibits the cleavage of SEQ ID NO:6 by BTA. In a test sample, any residual increase in fluorescence would be due to non-specific cleavage of the peptide.

TABLE I

Sequences and characterization of FRET peptides tested as substrates for BTA

| | Peptide Sequence | | | | | | | | | | | | | | | | SEQ ID NO: | FI/min |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | | | |
| | T | R | I | D | E | A | N | Q | R | A | T | K | M | L | | | SEQ ID NO:1 | NA |
| Abz | T | R | I | D | E | A | N | Q | R | A | T | K | X | D-K* | | | SEQ ID NO:2 | 37 |
| Abz | T | D-R | I | D | Q | A | N | Q | R | A | T | D-K | X | L | K* | | SEQ ID NO:3 | 1 |
| Abz | T | D-R | I | D | Q | A | N | Q | R | A | T | D-K | X | K* | | | SEQ ID NO:4 | 3 |
| Abz | T | D-R | I | D | E | A | N | Q | R | A | T | D-K | X | K* | | | SEQ ID NO:5 | 2 |
| Abz | T | D-R | I | D | E | A | N | Q | R | A | T | K | X | K* | | | SEQ ID NO:6 | 54 |
| Abz | T | D-R | I | D | Q | A | N | Q | R | A | T | K | X | K* | | | SEQ ID NO:7 | 32 |
| Abz | T | D-R | I | D | Q | A | N | Q | D-R | A | T | K | X | K* | | | SEQ ID NO:8 | 1 |
| Abz | T | D-R | I | D | Q | A | N | Q | R | A | T | K* | X | | | | SEQ ID NO:9 | 34 |
| Abz | T | D-R | I | D | E | A | N | Q | Y* | A | T | K | X | L | | | SEQ ID NO:10 | 0 |
| Abz | T | D-R | I | D | E | A | N | Q | R | A | T | K* | X | | | | SEQ ID NO:11 | 9 |

TABLE I-continued

Sequences and characterization of FRET peptides tested as substrates for BTA

| Peptide Sequence | SEQ ID NO: | FI/min |
|---|---|---|
| Mca T D-R I D E A N Q R A T K* X | SEQ ID NO:12 | 16 |
| Abz T D-R I D E A N Q R A T K* M | SEQ ID NO:13 | 6 |
| Abz T D-R I D E A N E R A T K* X | SEQ ID NO:14 | 0 |

NOTE:
SEQ ID NO:1 corresponds to residues number 190–203 of SNAP-25 and is for reference only.
Amino acid abbreviations are: T, threonine; R, arginine; I, isoleucine; D, aspartic acid; E, glutamic acid; A, alanine; N, asparagine; Q, glutamine, K, lysine, X, norleucine, D-R, D-arginine; D-K, D-lysine; M, methionine; L, leucine; Mca, (7-methoxycoumarin-4-yl)acetyl; K*, 2,4-dinitrophenyl-lysine; Abz, ortho-aminobenzoyl; Y*, 3-nitro-tyrosine.
FI/min is the change in fluorescence intensity (FI) per minute measured in arbitrary units. 7.5 µM of each FRET substrate was hydrolyzed by 9 nM BTA. FI was measured using an excitation bandwidth of 3 nm and an emission bandwidth of 10 nm.

TABLE II

Fluorescence intensities (FI) observed for 7.5 µM of the FRET peptides at 37° C.

| SEQ. ID. NO: | FI |
|---|---|
| SEQ ID NO:2 | 550 |
| SEQ ID NO:3 | 410 |
| SEQ ID NO:4 | 400 |
| SEQ ID NO:5 | 340 |
| SEQ ID NO:6 | 540 |
| SEQ ID NO:7 | 560 |
| SEQ ID NO:8 | 510 |
| SEQ ID NO:9 | 330 |
| SEQ ID NO:10 | 640 |
| SEQ ID NO:11 | 230 |
| SEQ ID NO:12 | 840 |
| SEQ ID NO:13 | 270 |
| SEQ ID NO:14 | 240 |

NOTE:
Fluorescence intensities (FI) were measured in Buffer A using an excitation bandwidth of 3 nm and an emission slit width of 10 nm. For all sequences except SEQ ID NO:12, $\lambda_{ex}$ was set to 326 nm and $\lambda_{em}$ to 423 nm. For SEQ ID NO:12, $\lambda_{ex}$ was set to 328 nm and $\lambda_{em}$ to 393 nm.

What is claimed is:

1. An isolated substrate peptide for determining the proteolytic activity of botulinum neurotoxin type A using intramolecularly quenched fluorescent detection, said substrate peptide consisting of at least 13 residues of amino acid, wherein said substrate peptide is selected from the group consisting of:

TD-RIDQANQRATKXK (SEQ ID NO. 7) and

TD-RIDQANQRATKX (SEQ ID NO. 9).

2. The substrate peptide of claim 1, wherein said substrate peptide is modified by attaching a fluorophore and a quencher group of fluorescence resonance energy transfer (FRET) thereon.

3. The substrate peptide of claim 2, wherein said fluorophore group is attached to the N-terminus of said substrate peptide.

4. The substrate peptide of claim 3, wherein said fluorophore group is ortho-aminobenzoyl.

5. The substrate peptide of claim 2, wherein said quencher group is 2,4-dinitrophenyl.

6. The substrate peptide of claim 5, wherein said quencher group in SEQ ID NO. 7 is attached to a residue of position 14.

7. The substrate peptide of claim 5, wherein said quencher group in SEQ ID NO. 9 is attached to a residue of position 12.

8. A kit for measuring botulinum type A toxin (BTA) in a sample, said kit comprising
  (i) a first container or containers having a positive control, wherein said control is botulinum type A toxin, a light chain of said toxin, or a protease;
  (ii) a second container or containers having a substrate peptide as claimed in claim 2;
  (iii) a third container or containers containing factors and buffers necessary for conducting a hydrolysis assay and
  (iv) a fourth container or containers containing inhibitors specific to said toxin for distinguishing hydrolysis by BTA.

* * * * *

SEQUENCE LISTING

<160> NUMBER OF SEQ ID NOS: 14

<210> SEQ ID NO 1
<211> LENGTH: 13
<212> TYPE: PRT
<213> ORGANISM: human

<400> SEQUENCE: 1

Thr Arg Ile Asp Glu Ala Asn Gln Arg Ala Thr Lys Met
1               5                   10

<210> SEQ ID NO 2
<211> LENGTH: 14
<212> TYPE: PRT
<213> ORGANISM: artificial sequence
<220> FEATURE:
<223> OTHER INFORMATION: synthetic peptide
<221> NAME/KEY: misc_feature
<222> LOCATION: (13)..(13)
<223> OTHER INFORMATION: Leu represents norleucine
<221> NAME/KEY: misc_feature
<222> LOCATION: (14)..(14)
<223> OTHER INFORMATION: Xaa represents D-Lys

<400> SEQUENCE: 2

Thr Arg Ile Asp Glu Ala Asn Gln Arg Ala Thr Lys Leu Xaa
1               5                   10

<210> SEQ ID NO 3
<211> LENGTH: 15
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (12)..(12)
<223> OTHER INFORMATION: Xaa represents D-Lys
<221> NAME/KEY: misc_feature
<222> LOCATION: (13)..(13)
<223> OTHER INFORMATION: Leu represents norleucine

<400> SEQUENCE: 3

Thr Xaa Ile Asp Gln Ala Asn Gln Arg Ala Thr Xaa Leu Leu Lys
1               5                   10                  15

<210> SEQ ID NO 4
<211> LENGTH: 14
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (12)..(12)
<223> OTHER INFORMATION: Xaa represents D-Lys
<221> NAME/KEY: misc_feature
<222> LOCATION: (13)..(13)
<223> OTHER INFORMATION: Leu represents norleucine

<400> SEQUENCE: 4

Thr Xaa Ile Asp Gln Ala Asn Gln Arg Ala Thr Xaa Leu Lys
1               5                   10

<210> SEQ ID NO 5
<211> LENGTH: 14
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (12)..(12)
<223> OTHER INFORMATION: Xaa represents D-Lys
<221> NAME/KEY: misc_feature
<222> LOCATION: (13)..(13)
<223> OTHER INFORMATION: Leu represents norleucine

<400> SEQUENCE: 5

Thr Xaa Ile Asp Glu Ala Asn Gln Arg Ala Thr Xaa Leu Lys
1               5                   10

<210> SEQ ID NO 6
<211> LENGTH: 14
<212> TYPE: PRT
<213> ORGANISM: artificial sequence
<220> FEATURE:
<223> OTHER INFORMATION: synthetic peptide

```
<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 6

Thr Xaa Ile Asp Glu Ala Asn Gln Arg Ala Thr Lys Leu Lys
1               5                   10

<210> SEQ ID NO 7
<211> LENGTH: 14
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 7

Thr Xaa Ile Asp Gln Ala Asn Gln Arg Ala Thr Lys Leu Lys
1               5                   10

<210> SEQ ID NO 8
<211> LENGTH: 14
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (9)..(9)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 8

Thr Xaa Ile Asp Gln Ala Asn Gln Xaa Ala Thr Lys Leu Lys
1               5                   10

<210> SEQ ID NO 9
<211> LENGTH: 13
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 9

Thr Xaa Ile Asp Gln Ala Asn Gln Arg Ala Thr Lys Leu
1               5                   10

<210> SEQ ID NO 10
<211> LENGTH: 14
<212> TYPE: PRT
<213> ORGANISM: artificial sequence
<220> FEATURE:
<223> OTHER INFORMATION: synthetic peptide
```

<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 10

Thr Xaa Ile Asp Glu Ala Asn Gln Tyr Ala Thr Lys Leu Leu
1               5                   10

<210> SEQ ID NO 11
<211> LENGTH: 13
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 11

Thr Xaa Ile Asp Glu Ala Asn Gln Arg Ala Thr Lys Leu
1               5                   10

<210> SEQ ID NO 12
<211> LENGTH: 13
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine

<400> SEQUENCE: 12

Thr Xaa Ile Asp Glu Ala Asn Gln Arg Ala Thr Lys Leu
1               5                   10

<210> SEQ ID NO 13
<211> LENGTH: 13
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg

<400> SEQUENCE: 13

Thr Xaa Ile Asp Glu Ala Asn Gln Arg Ala Thr Lys Met
1               5                   10

<210> SEQ ID NO 14
<211> LENGTH: 13
<212> TYPE: PRT
<213> ORGANISM: artificial sequence
<220> FEATURE:
<223> OTHER INFORMATION: synthetic peptide
<221> NAME/KEY: misc_feature
<222> LOCATION: (2)..(2)
<223> OTHER INFORMATION: Xaa represents D-Arg
<221> NAME/KEY: misc_feature
<222> LOCATION: (13)..(13)
<223> OTHER INFORMATION: Leu represents norleucine -continued

```
<400> SEQUENCE: 14

Thr Xaa Ile Asp Glu Ala Asn Glu Arg Ala Thr Lys Leu
1               5                   10
```